US006405601B1

United States Patent
Yang

(10) Patent No.: US 6,405,601 B1
(45) Date of Patent: Jun. 18, 2002

(54) METHOD OF ESTIMATING HOLD TIME SWEEP CRACK GROWTH PROPERTIES

(75) Inventor: Ling Yang, Clifton Park, NY (US)

(73) Assignee: General Electric Company, Schenectady, NY (US)

( * ) Notice: Subject to any disclaimer, the term of this patent is extended or adjusted under 35 U.S.C. 154(b) by 27 days.

(21) Appl. No.: 09/742,446

(22) Filed: Dec. 22, 2000

(51) Int. Cl.$^7$ .............................................. G01N 19/08
(52) U.S. Cl. .................................................... 73/799
(58) Field of Search ....................... 73/799, 802, 804, 73/805, 806, 808

(56) References Cited

U.S. PATENT DOCUMENTS

| | | | | |
|---|---|---|---|---|
| 4,685,977 A | * | 8/1987 | Chang | 148/410 |
| 4,957,567 A | * | 9/1990 | Krueger et al. | 148/410 |
| 6,063,212 A | * | 5/2000 | Cabral | 148/410 |

* cited by examiner

Primary Examiner—Max Noori
(74) Attorney, Agent, or Firm—Banner & Witcoff, Ltd.

(57) ABSTRACT

A method to estimate the crack growth rate of HIPed cast IN718 material with various grain sizes and working environments comprising determining the average grain size diameter and duration of hold time and solving the following equation, $$\frac{da}{dN} = \frac{1}{1.19 \times 10^5 \times GS + 5.59 \times 10^4 \times Env - 1.17 \times 10^5 \times GS \times Env + 0.66 \times HT - 7.267 \times GS \times HT}$$

whereby N is the number of operating cycles, a is the crack length, da/dN is crack growth rate GS is the average grain size in meters, HT is hold time in seconds, Env is 1 for an air environment, and Env is −1 if a steam environment. The estimates obtained from the transfer function can be used for designing of and predicting the life of cast IN718 components such as manifolds.

5 Claims, 1 Drawing Sheet

METHOD OF ESTIMATING HOLD TIME SWEEP CRACK GROWTH PROPERTIES

BACKGROUND OF THE INVENTION

1. Field of the Invention

This invention relates to a method for estimating hold time sweep crack growth properties of IN718 cast HIPed material.

2. Description of the Prior Art

Inconel Alloy 718 (IN718) has the major chemistry of Ni—Fe—Cr—Cb—Mo—Ti—Al and was developed through extensive optimization studies by H. L. Eiselstein at the International Nickel Company (INCO) in the 1950's. Alloy IN718 is a precipitation hardenable nickel based alloy with high strength and ductility at temperatures up to 704° C., good corrosion resistance, ease of formability and can be welded with good resistance to strain-age cracking. Alloy IN718 was initially developed for the aerospace industry, and it has been used for jet engine and high-speed airframe parts such as wheels, buckets, spacers, and high temperature bolts and fasteners. IN718 investment cast HIPed material is a new approach in making manifold for steam delivery system in GE H technology gas turbines.

Investment casting, often called lost wax casting, is regarded as a precision casting process to fabricate near-net-shaped metal parts from almost any alloy. The most common use of investment casting in more recent history has been the production of components requiring complex, often thin-wall castings. The investment casting process normally includes the following steps: creating a wax pattern, assembling the wax pattern cluster, "investing" the cluster with ceramic stucco/slurry; de-waxing and fire molding the ceramic for strength, melting the alloy in vacuum or air; pouring molten alloy into the mold; knocking off the shell and heat treating/machining/coating operations. An HIP process (Hot Isostatic Pressing) sometimes follows the investment casting process to consolidate shrinkage porosity internal to casting and help homogenize structure.

GE Power Systems introduced H technology gas turbines in 1995. H technology is a platform of combined-cycle technology that integrates the gas turbine, steam turbine and generator into a seamless system, where each component is optimized for the highest level of performance. The centerpiece of this new technology platform is an advanced closed-loop steam cooling system in the gas turbine which permits higher firing temperature while retaining combustion temperatures at levels consistent with low emissions. That will enable the new machines to operate at firing temperatures in the 2,600F. class, leading to 60% net thermal efficiency and world record output for a combined-cycle unit. Unlike aircraft engines, which only have air for cooling, a combined-cycle system has ready steam supply. That steam is captured and used for cooling in this closed-loop system. Steam is desired because it has a higher heat capacity than air. The steam cooling system uses a manifold as a critical component. However, it is difficult to make the manifold due to its complex geometry. See FIG. 1.

Originally, manifolds were made by machining forged alloy IN718 material to the desired shape. This process can be expensive and take a long time. Other processes were investigated to reduce the cost and cycle time including the HIPed (Hot Isostatic Press) investment casting process. Manifolds produced by the investment cast process of alloy IN718 have lower costs, larger yields and reduced cycle time.

However, in designing a manifold, hold time sweep crack growth rate must be considered. It is fatal to have fast crack growth rate for manifold with thin walls. Because the crack growth rate was unknown for superalloy IN718 material formed by the HIPed investment cast process, it has been difficult to design manifolds with this material. Moreover, the manifold is working in steam environment and the effect of steam on hold time crack growth rate was also unknown.

Crack growth rate can be affected by many factors such as process parameters, grain size, hold time, and temperature. Materials made by investment casting can have varied grain sizes. For example, thin sections or areas close to the mold can have fine grains, while the center of thick sections can have coarse grain size. Forging, on the other hand, typically has uniform grain size all over the part. In addition, duration of hold time, and the type of environment (steam or air) can also affect the crack growth rate.

The relationship between HIPed investment cast IN718 hold time crack growth rate properties and the corresponding grain size, environment, and hold time length is desirable for the design and life evaluation of a manifold. However, hold time sweep crack growth rate data was heretofore not available for cast HIPed 718 material, and there was no known method to estimate the crack growth rate. Moreover the effect of steam on the cast HIPed 718 material with various grain sizes was unknown.

BRIEF SUMMARY OF THE INVENTION

The invention relates to a method to estimate the crack growth rate of HIPed cast IN718 material with various grain sizes and working environments. In particular, the invention is directed to a method of estimating the crack growth rate of an HIPed IN718 investment cast component in an air or steam environment comprising determining the average grain size diameter and duration of hold time and solving the following equation, $$\frac{da}{dN} = \frac{1}{1.19 \times 10^5 \times GS + 5.59 \times 10^4 \times Env - 1.17 \times 10^5 \times GS \times Env + 0.66 \times HT - 7.267 \times GS \times HT}$$

whereby N is the number of operating cycles, a is the crack length, da/dN is crack growth rate, GS is the average grain size in meters, HT is hold time in seconds, Env is 1 for an air environment, and Env is −1 for a steam environment.

The estimates obtained from the transfer function can be used for designing of and predicting the life of cast IN718 components such as manifolds.

DETAILED DESCRIPTION OF THE INVENTION

Figure 1:
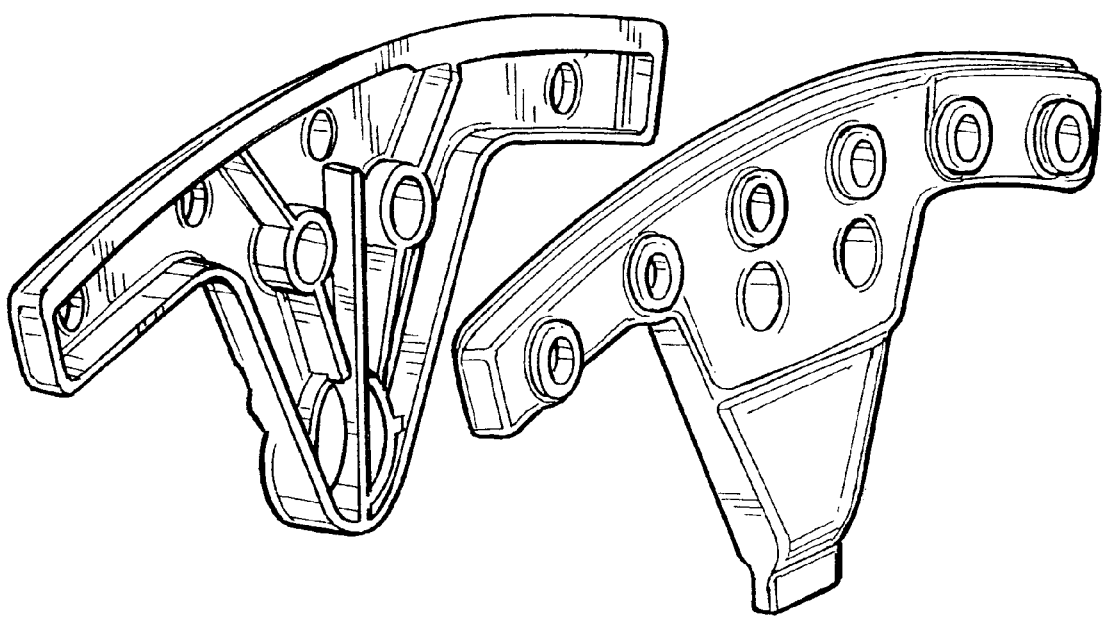
FIG. 1 depicts a manifold.

It was discovered that a relationship existed between crack growth rate and the corresponding grain size of HIPed investment cast IN718 components. The relationship depends on whether the manifold is operated under an air or steam environment. When the grain size range of the manifold is known, the crack growth rate can be estimated. This relationship is important in designing of and predicting the life of the cast components. These relationships are important in designing of and predicting the life of the cast components such as manifolds. The relationships are also important in other cast processes such as for the formation of elbows in steam delivery systems. The development of these relationships are described below.

As can be seen in FIG. 1, a manifold has thin walls and a complex geometry making it difficult to machine tensile specimens from the manifold in order to test its properties. Therefore, in order to obtain accurate data easily, slabs of IN718 having a simple geometry were made and tested. Several different superheat temperatures and mold sizes were applied to the slabs to obtain slabs having three different grain diameters, 0.125", 0.050" and 0.029" respectively. This grain size range covers the normal range encountered in manifold production

| Slab ID | Superheat (F.) | Mold Size | Average Grain Size (") |
|---|---|---|---|
| 1 | 30 | 6.0" × 3.1" × 1.0" | 0.125 |
| 2 | 30 | 4.4" × 4.0" × 0.68"* | 0.050 |
| 3 | 20 | 4.4" × 4.0" × 0.68"* | 0.029 |

*Slab with thinner section in center (grain size in thicker edge sections was 0.050 and in the thinner center section was 0.029").

Multiple specimens were taken from each slab, and hold time crack growth tests were performed at temperatures of 593° C. (1100° F.). This temperature represented the high operating temperature of the manifold. Tests were conducted under the same conditions in both air and steam environments. Results on crack growth rates da/dN (increase of crack length per cycle, in the unit of inch/cycle) were recorded and analyzed by statistic software Minitab. Sampling Data used to develop the relationship is depicted in the table below.

| GS | Env | Hold Time | da/dN |
|---|---|---|---|
| 0.125 | Air | 100 | 5.60E−06 |
| 0.125 | Steam | 100 | 2.83E−06 |
| 0.125 | Air | 3600 | 2.39E−05 |
| 0.125 | Steam | 3600 | 3.90E−06 |
| 0.05 | Air | 100 | 7.80E−06 |
| 0.05 | Steam | 100 | 1.21E−05 |
| 0.05 | Air | 3600 | 4.89E−05 |
| 0.05 | Steam | 3600 | 2.17E−05 |
| 0.029 | Air | 100 | 9.22E−05 |
| 0.029 | Steam | 100 | 2.03E−04 |
| 0.029 | Air | 3600 | 5.60E−03 |
| 0.029 | Steam | 3600 | 9.50E−02 |

From the results, it was observed that (1) cracks grow faster when the grain size is finer and da/dN follows reciprocal relation with grain size; and (2) cracks grow faster in steam environments than in air environments.

The following transfer function was developed from the data. N denotes operating cycles and a is the crack length. da/dN is the growth of crack length per unit cycle.

$$\frac{da}{dN} = \frac{1}{4.68 \times 10^6 \times GS + 5.59 \times 10^4 \times Env - 1.17 \times 10^5 \times GS \times Env + 0.66 \times HT - 286.1 \times GS \times HT}$$

GS is the average diameter of the grains (inch), HT is the duration of hold time in seconds, Env of 1 represents an air environment and Env of −1 represents a steam environment. The transfer functions were then converted to metric units.

$$\frac{da}{dN} = \frac{1}{1.19 \times 10^5 \times GS + 5.59 \times 10^4 \times Env - 1.17 \times 10^5 \times GS \times Env + 0.66 \times HT - 7.267 \times GS \times HT}$$

whereby N is the number of operating cycles, a is the crack length, da/dN is crack growth rate, GS is the average grain size in meters, HT is hold time in seconds, Env is 1 for an air environment, and Env is −1 if a steam environment.

When the grain size of the cast HIPed IN718 material and operating environment are known, crack growth rate for certain hold times at 593° C. (1100° F.) can be determined from the above mentioned transfer function.

In order to confirm that the transfer function provided accurate results, compact tension specimens were taken from an actual cast manifold and grain sizes were measured for each specimen. These samples were tested at the same conditions as the slab specimens. The results showed that the transfer function provided accurate results.

This method can determine the crack growth rate at high temperature for the design of the HIPed investment IN718 casting manifold or any other component made of HIPed cast IN718. Given a certain grain size, the crack growth rate of different hold time at high temperature can be estimated. Moreover, the difference in the crack growth rates in air and steam environment can be compared.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method of estimating the crack growth rate of an HIPed IN718 cast component in an air or steam environment comprising determining the average grain size diameter and duration of hold time at about 593° C. and solving the following equation, $$\frac{da}{dN} = \frac{1}{1.19 \times 10^5 \times GS + 5.59 \times 10^4 \times Env - 1.17 \times 10^5 \times GS \times Env + 0.66 \times HT - 7.267 \times GS \times HT}$$

whereby N is the number of operating cycles, a is the crack length, da/dN is crack growth rate, GS is the average grain size in meters, HT is hold time in seconds, Env is 1 for an air environment, and Env is −1 if a steam environment.

2. The method of claim 1 wherein the cast component is a manifold.

3. The method of claim 1 wherein the crack growth rate is estimated for a steam environment and Env is −1.

4. The method of claim 1 wherein the crack growth rate is estimated for an air environment and Env is 1.

5. The method of claim 1 wherein the cast component is an investment cast component.

* * * * *